US006322567B1

(12) United States Patent
Mittelstadt et al.

(10) Patent No.: US 6,322,567 B1
(45) Date of Patent: Nov. 27, 2001

(54) BONE MOTION TRACKING SYSTEM

(75) Inventors: Brent D. Mittelstadt, Placerville; Steven M. Cohan, Woodland, both of CA (US)

(73) Assignee: Integrated Surgical Systems, Inc., Davis, CA (US)

(*) Notice: Subject to any disclaimer, the term of this patent is extended or adjusted under 35 U.S.C. 154(b) by 0 days.

(21) Appl. No.: 09/247,818

(22) Filed: Feb. 9, 1999

Related U.S. Application Data

(60) Provisional application No. 60/112,319, filed on Dec. 14, 1998.

(51) Int. Cl.$^7$ .................................................. A61B 19/00

(52) U.S. Cl. ................................................................ 606/130

(58) Field of Search ........................ 606/130, 1; 600/425, 600/426, 427, 429; 128/922

(56) References Cited

U.S. PATENT DOCUMENTS

| 4,146,924 | 3/1979 | Birk et al. ............................. 364/513 |
|---|---|---|
| 4,373,532 | 2/1983 | Hill et al. ............................. 128/660 |
| 4,841,975 | 6/1989 | Woolson ............................... 128/653 |
| 4,932,414 | 6/1990 | Coleman et al. ..................... 128/660 |
| 4,945,914 | 8/1990 | Allen .................................... 128/653 |
| 4,991,579 | 2/1991 | Allen .................................... 128/653 |
| 5,016,639 | 5/1991 | Allen .................................... 128/653 |
| 5,086,401 | 2/1992 | Glassman et al. .................... 395/94 |
| 5,094,241 | 3/1992 | Allen .................................... 128/653 |
| 5,097,839 | 3/1992 | Allen .................................. 128/653.1 |
| 5,119,817 | 6/1992 | Allen .................................. 128/653.1 |
| 5,142,930 | 9/1992 | Allen et al. ........................... 74/469 |
| 5,161,536 | 11/1992 | Vilkomerson et al. ............. 128/660 |
| 5,167,165 | 12/1992 | Brucher et al. ....................... 74/479 |
| 5,178,164 | 1/1993 | Allen .................................... 128/898 |

(List continued on next page.)

FOREIGN PATENT DOCUMENTS

| 647 428 A2 | 12/1995 | (EP) ........................................... 6/12 |
|---|---|---|
| 0647428 A | 4/1995 | (EP) ...................................... 606/130 |
| WO 91/07726 | 5/1991 | (WO) ....................................... 15/72 |
| WO 94/17733 | 8/1994 | (WO) ......................................... 6/12 |
| WO 97/09929 | 3/1997 | (WO) .................................. 606/130 |

OTHER PUBLICATIONS

Ault, et al., "Frameless patient registration using ultrasonic imaging", The Robotics Institute, School of Computer Science, Pittsburgh, Pennsylvania, pp. 74–81.

Cain, et al., "Safety considerations in a surgical robot", Integrated Surgical Systems, Inc., Sacramento, California, Paper #93–035, pp. 291–294, (1993).

Champleboux et al., "An optical conformer for radiotherapy treatment planning", TIMC–IMAG, Faculté de Médecine de Grenoble, La Tronche, France, pp. 69–73.

Grimson, et al., "Automated registration for enhanced reality visualization in surgery", Visualization in Surgery, pp. 82–89.

Kazanzides, et al., "Surgical and industrial robots: Comparison and case study", Integrated Surgical Systems, Inc., Sacramento, California, vol. 10, pp. 10–19 to 10–26 (circa 1994).

(List continued on next page.)

Primary Examiner—David O. Reip
Assistant Examiner—(Jackie) Tan-Uyen T. Ho
(74) Attorney, Agent, or Firm—Townsend and Townsend and Crew LLP

(57) ABSTRACT

A method of tracking and compensating for bone motion when operating on bone (50) with surgical robotic arm (20), comprising: determining a spatial relationship between surgical robotic arm (20) and bone (50); tracking translational and rotational movements of bone (50) with a bone motion detector, which preferably comprises a passive mechanical arm (40); and updating the spatial relationship as bone (50) moves.

22 Claims, 4 Drawing Sheets

U.S. PATENT DOCUMENTS

| | | | |
|---|---|---|---|
| 5,180,382 | * | 1/1993 | Frigg et al. . |
| 5,198,877 | | 3/1993 | Schulz ................................. 356/375 |
| 5,211,164 | | 5/1993 | Allen ................................ 128/653.1 |
| 5,222,499 | | 6/1993 | Allen et al. ....................... 128/653.1 |
| 5,230,338 | | 7/1993 | Allen et al. ........................... 128/653 |
| 5,236,432 | | 8/1993 | Matsen et al. ......................... 606/88 |
| 5,249,581 | | 10/1993 | Horbal et al. ........................ 128/664 |
| 5,299,288 | | 3/1994 | Glassman et al. ................... 606/130 |
| 5,306,306 | | 4/1994 | Bisek et al. ............................ 623/16 |
| 5,320,115 | | 6/1994 | Kenna ................................. 128/898 |
| 5,343,877 | | 9/1994 | Park ..................................... 128/898 |
| 5,383,454 | | 1/1995 | Bucholz ............................ 128/653.1 |
| 5,394,457 | * | 2/1995 | Leibinger et al. . |
| 5,394,875 | | 3/1995 | Lewis et al. .................... 128/660.09 |
| 5,397,329 | | 3/1995 | Allen ..................................... 606/73 |
| 5,408,409 | | 4/1995 | Glassman et al. ............. 364/413.13 |
| 5,411,503 | | 5/1995 | Hollstein et al. ...................... 606/86 |
| 5,480,400 | | 1/1996 | Berger .................................. 606/60 |
| 5,524,180 | | 6/1996 | Wang et al. ......................... 600/118 |
| 5,546,942 | | 8/1996 | Zhang ............................... 128/653.1 |
| 5,564,437 | | 10/1996 | Bainville et al. .................... 128/774 |
| 5,590,215 | | 12/1996 | Allen .................................... 382/128 |
| 5,649,021 | | 7/1997 | Matey et al. ......................... 382/128 |
| 5,674,221 | * | 10/1997 | Hein et al. . |
| 5,682,886 | | 11/1997 | Delp et al. ........................ 128/653.1 |
| 5,696,837 | | 12/1997 | Green .................................. 382/128 |
| 5,769,078 | * | 6/1998 | Kliegis . |
| 5,772,594 | * | 6/1998 | Barrick . |
| 5,806,518 | | 9/1998 | Mittelstadt ........................ 128/653.1 |
| 5,807,252 | * | 9/1998 | Hassfeld et al. . |
| 5,824,085 | * | 10/1998 | Sahay et al. . |
| 5,868,675 | * | 2/1999 | Henrion et al. . |

OTHER PUBLICATIONS

Kazanzides, et al., "Architecture of a surgical robot", IEEE Conference on Systems, Man, and Cybernetics, pp. 1624–1629, (1992).

Kazanzides, et al., "Force sensing and control for surgical robot", IEEE Intl. Conference on Robotics and Automation, pp. 612–617, (May 1992).

Lea, et al., "Registration and immobilization for robot–assisted orthopaedic surgery", Department of Mechanical Engineering, Northwestern University, Evanston, Illinois, pp. 63–68.

Lavallee, et al., "Computer assisted spine surgery: A technique for accurate transpedicular screw fixation using CT data and a 3–D optical localizer", TIMC, Faculte de Medecine de Grenoble, La Tronche, France, pp. 315–322 (1995).

Lombardi, Adolph V., "Cement removal in revision total hip arthroplasty", Seminars in Arthroplasty, 3(4):264–272, (Oct. 1992).

Mittelstadt et al., "Robotic surgery: Achieving predictable results in an unpredictable environment", Integrated Surgical Systems, Inc., Sacramento, California, pp. 367–372, (1993).

Mittelstadt et al., "The evolution of a surgical robot from prototype to human clinical use", Integrated Surgical Systems, Inc., Sacramento, California, pp. 36–41, (1994).

Mittelstadt et al., "Development of a surgical robot for cementless total hip replacement", Robotics, 11:553–560, (1993).

Nolte, et al., "A novel approach to computer assisted spine surgery", M.E. Muller Institute for Biomechanics, University of Bern, Bern, Switzerland a pp. 323–328 (1995).

Paul et al., "Development of a surgical robot for cementless total hip arthroplasty", Clinical Orthopaedics, 285:57–66, (1992).

Potamianos et al., "Intra–operative imaging guidance for keyhole surgery methodology and calibration", Robotics Group, Imperial College of Science, Technology and Medicine, London, United Kingdom, pp. 98–104.

Péria et al., "Accurate registration of SPECT and MR brain images of patients suffering from epilepsy or tumor", TIMB--TIMC–IMAG, Faculte de Medecine de Grenoble, La Tronche, France pp. 58–62.

Simon, et al., "Techniques for fast and accurate intra–surgical registration", Robotics Institute, Carnegie Mellon University, Pittsburgh, Pennsylvania, pp. 90–97.

* cited by examiner

BONE MOTION TRACKING SYSTEM

This application claims the benefit and priority of U.S. patent application Ser. No. 60/112,319, filed Dec. 14, 1998. The full disclosure of which is hereby incorporated by reference for all purposes.

TECHNICAL FIELD

The present invention relates to surgical bone cutting systems and more particularly to systems for detecting or tracking bone motion during surgery.

BACKGROUND OF THE INVENTION

When performing robotically assisted total hip replacement surgery, (for example, when cutting a cavity into a patient's femur bone for the insertion of an artificial hip joint therein), it is very important to minimize the effects of bone motion. Successful hip replacement surgery, particularly when using cementless implants, relies on the highly accurate creation of the cavity within the proximal (upper) end of the femur for receiving the implant. Deviations of less than plus or minus 1 mm from the planned cavity placement and dimensions are desirable.

Accordingly, to minimize the effects of unwanted bone motion on cutting accuracy, it has been desirable to attempt to prevent bone motion to the maximum degree possible by firmly anchoring the bone while the surgical bone cutter is operating on the bone. Typically, unwanted bone motion has been restrained by the use of fixators which hold the bone in position as firmly as is possible. Unfortunately, there are practical limits as to how securely the bone can be held in position by a fixator. For example, for many surgical procedures it is necessary for the surgical team to hand hold retractors for surgical access. Changes in the forces applied to the bone by these hand held retractors can cause unwanted bone motion. Moreover, in many cases the surgical team does not know whether additional retraction is required until after the bone cutting procedure has commenced. As such, it is typically necessary to modify or slightly change the retraction forces on the bone during the course Of the bone surgery. This can have the undesirable effect of causing unwanted bone motion, leading to inaccuracies in cutting the bone. In addition, under some conditions, such as to provide optimal cutting access, it may even be desirable to move the bone slightly during surgery. This further complicates the problem of cutting inaccuracies caused by unwanted bone motion thereafter.

Small amounts of bone motion cause the surgical operative site to "drift", thereby causing undesirable implant cavity placement errors as the bone moves while a robotic bone cutter is cutting the implant cavity in the bone. Larger amounts of bone motion can cause serious cutting inaccuracies and are indicative of the bone fixation or retraction system becoming unstable. Should such larger amounts of bone motion occur, it is then necessary to immediately shut down the cutting operation and restart the cutting procedure after re-locating the position of the bone with respect to the cutting device. Specifically, the surgical team is required to remove the cutting device and its accompanying gas supply hose and irrigation, re-determine the position of the bone with respect to the cutting device, and then reinstall the cutter, gas supply, and irrigation systems before continuing with the bone cutting procedure. This can be very time consuming and frustrating for the surgical team.

SUMMARY OF THE INVENTION

As discussed above, unwanted bone motion can generate cutting inaccuracies during bone surgery. Such unwanted bone motion cannot be completely eliminated during bone surgery. Accordingly, the present invention provides a system to minimize the effects of unwanted bone motion by tracking the motion of the bons such that the unwanted bone motion can be compensated for in real time during surgery on the bone.

In a preferred aspect, the present invention provides a method of tracking and compensating for bone motion when operating on a bone with a surgical robotic cutting arm, comprising; initially registering the surgical robotic cutting arm to the bone (ie: determining the initial spatial relationship between the surgical robotic cutting arm and the bone), tracking bone motion with a bone motion detector; and compensating for the bone motion by updating the registration between the surgical robotic cutting arm and the bone as the bone moves. (Initially registering the surgical robotic cutting arm to the bone comprises determining the initial spatial relationship between the surgical robotic cutting arm and the bone such that the surgical robotic arm can be positioned to operate at a desired location or locations on the bone).

In certain preferred aspects, the system of tracking bone motion includes tracking both translational and rotational movements of the bone with a bone motion detector. In alternate preferred aspects, the system of tracking bone motion includes tracking only translational movements of the bone with a bone motion detector.

An important advantage of the present invention is that compensation for bone motion is made during surgery such that the surgical team is not forced to terminate the cutting procedure, re-register the surgical robotic arm to the bone, and then re-start the cutting procedure each time the bone moves. Instead, the present system enables the surgical robotic arm to continue to accurately cut the cavity into the bone, even during bone motion.

Determining the initial spatial relationship between the surgical robotic arm and the bone can be accomplished in a variety of ways using radio-opaque marker pins. For example, prior to surgery, the marker pins are attached to the bone and a pre-surgical image of the bone with the marker pins attached is taken. The pre-surgical image can preferably be generated by computerized tomography (CT), digital radiography, or the like. From the pre-surgical image, the spatial relationship of the bone with respect to the marker pins can be determined, (ie: the position and orientation of the bone can be determined by knowing the position and orientation of the marker pins). Thereafter, the surgical robotic arm is registered to the bone by being moved to contact each of the marker pins in turn. As such, the position of each of the marker pins will be sequentially recorded in terms of the surgical robotic arm's co-ordinate system, thereby registering the surgical robotic arm to the bone.

An advantage of this registration method is that bone motion can be detected as the surgical robotic arm is initially registered to the bone, as follows. The spacing of the marker pins with respect to one another is initially determined at the time when these marker pins are first viewed in the pre-surgical image of the bone. As the surgical robotic arm is brought into contact with each of these marker pins in turn during the registration process, bone motion detection is achieved by observing any apparent deviations in the relative spacing among the various marker pins. In particular, should the relative spacing between a first and a second marker pin be found to be different from that which was initially observed in the bone image, this would indicate bone motion during the interval of time during which the surgical robotic arm is moved from contacting the first marker pin to contacting the second marker pin. The detection of such bone motion during initial registration can be used to shut down the registration process such that the bone can be re-stabilized prior to re-commencement of the registration process.

Alternatively, when tracking bone motion with a bone motion detection system during the initial registration of the surgical robotic arm to the bone, (for example, by tracking bone motion with a passive mechanical arm secured at its distal end to the bone), the registration process need not be interrupted and re-started, even if bone motion occurs during the initial registration process, as will be explained.

Since the marker pins remain at fixed locations on the bone as the bone moves, an advantage of the above marker pin approach to registering the surgical robotic arm to the bone is that only the position of the marker pins needs to determined with respect to the surgical robotic arm, (subsequent to determining the position of the marker pins with respect to the bone).

Another advantage of the above approach to registering the surgical robotic cutting arm to the bone is that bone motion can be detected without having to track the successive movement of the marker pins. Rather, as will be explained, the marker pins are only used when initially registering the surgical robotic arm to the bone.

Alternatively, the surgical robotic arm can be registered to the bone using marker pins by the system described in co-pending application Ser. No. 09/022,643, which describes a method and system for transforming a bone image into a robotic coordinate system based upon registering between the robotic coordinate system and the image data set: (1) two positional coordinates axially spaced apart along the bone and (2) a directional vector passing through at least one of the positional coordinates.

In alternate approaches, the surgical robotic arm can be registered to the bone without the use of marker pins. For example, the initial position and orientation of the bone may be determined by an imaging system which relies upon sensing anatomical features of the bone. Such an imaging system may comprise an optical or ultrasound system which views the shape and location of the bone.

Alternatively, the surgical robotic arm can be registered to the bone without the use of marker pins by the system described in co-pending and recently allowed application Ser. No. 08/526,826 in which a bone image is transformed into a robotic coordinate system by aligning a robotic probe within the medullary canal of the femur.

Alternatively, the surgical robotic arm can be registered to the bone without the use of marker pins by the system described in co-pending application Ser. No. 09/152,359 which describes a method and system for transforming a bone image data set representing a bone image into a robotic coordinate system by registering a bone digitizer arm to the robotic coordinate system, generating a digitized bone data set by taking bone surface position measurements with the digitizer arm, and transforming the bone image data set into the robotic coordinate system by performing a best fit calculation between coordinates of the bone image data set and corresponding coordinates of the digitized bone data set.

The bone digitizer arm may comprise the passive mechanical arm described herein, (which is preferably used for measuring bone motion), or alternatively, may comprise a separate additional mechanical arm which is registered to the robotic coordinate system.

Accordingly, the present invention can be used either with marker pin registration systems or with pinless registration systems which rely on anatomic images of the bone prior to, and during, surgery.

In a preferred aspect of the present invention, tracking translational and rotational movements of the bone with the bone motion detector may include securing a distal end of a six degree of freedom passive mechanical arm to the bone and tracking movement of the passive mechanical arm as it moves with the bone. (As used herein, a six degree of freedom system is understood to refer to any system which senses translational movement along three mutually perpendicular axes and senses rotational movement around each of the three mutually perpendicular axes.) In a preferred aspect, the distal end of the passive mechanical arm is secured to the bone by a coupling member which is percutaneously attached to the bone. The proximal end of the passive mechanical arm is preferably secured at a fixed location in the coordinate system of the surgical robotic arm. In particular, the proximal end of the passive mechanical arm is preferably secured to the frame of a robotic workstation from which the surgical robotic arm also extends. Being secured to the same fixture, relative motion between the coordinate systems of the surgical robotic arm and the passive mechanical arm is prevented.

In a preferred aspect of the invention, the passive mechanical arm comprises an articulated linkage having high resolution position sensors at each joint. Using an embedded processor and appropriate software, the passive mechanical arm produces an accurate measurement of the position of its distal end relative to its proximal end.

(It is to be understood that the present passive mechanical arm may be substituted by a powered mechanical arm performing the same functions as described herein.)

Since the bone, (and the attached distal end of the passive mechanical arm), moves together as a solid unit, the passive mechanical arm accurately tracks bone motion regardless of where it is secured to the bone. Accordingly, the passive mechanical arm is preferably secured to the bone at a location some distance away from the operating site of the surgical robot arm such that the passive mechanical arm does not interfere with the operation of the surgical robotic cutting arm. Having six degrees of freedom of movement, the passive mechanical arm is adapted to move in three mutually perpendicular translational directions and is also adapted to rotate about three mutually perpendicular axes. As the bone moves, the distal end of the passive mechanical arm secured to the bone will also move. By tracking both the translational and rotational movement of the distal end of the passive mechanical arm secured to the bone, the translational and rotational movement of the bone is determined.

It is to understood that instead of tracking bone motion in six degrees of freedom, bone motion detection by the passive mechanical arm can also be limited to three degrees of motion if desired. For example, bone motion detection can be limited to detecting movement of the bone by tracking movement of the distal end of the passive mechanical arm along three mutually perpendicular translational axes.

The position and orientation of the passive mechanical arm is preferably monitored continuously or in very short intervals of time, (such as 10 to 100 times per second), such that bone motion can be very quickly detected and compensated for in real time such that only minimal changes to the spatial relationship between the surgical robotic arm and the bone need to be made, thereby reducing the potential for cutting inaccuracies.

It is to be understood that the present bone motion tracking system is not limited to a passive mechanical arm secured at one end to the bone, but may alternatively include optical sensors, (such as the OPTOTRACK™ system, produced by Northern Digital of Waterloo, Ontario, Canada), ultrasound, or laser tracking systems.

In the present invention, registration between the surgical robotic arm and the bone is updated when the bone motion detector has detected bone movement above a first threshold amount. This first threshold of movement is preferably pre-set to be a very small, such as on the order of ½ mm for translational movement or ½ degree for rotational movement. Should the bone motion exceed the first pre-set threshold amount of movement, the spatial relationship between the surgical robotic arm and the bone will be updated to compensate for bone motion, thus avoiding bone cutting errors. Optionally as well, when updating the registration of the surgical robotic arm to the bone, the cutting operation of the surgical robotic arm will be paused.

Bone motion below this first threshold amount need not be compensated for, due to its very minimal amount. However, for bone motion above this first threshold, the registration between the surgical robotic arm and the bone is automatically updated. Such updating of the registration is preferably performed at a near-continuous rate such that unwanted bone motion is rapidly detected and compensated for during bone cutting. Most preferably, such updating is preferably performed at the same rate at which the position and orientation of the passive mechanical arm is monitored, (preferably 10 to 100 times per second).

Should bone motion bee detected which is greater than a second pre-set threshold of movement (the second threshold of movement being greater than the first threshold of movement), the surgical robotic arm will immediately cease operation, since such a large degree of bone motion would seem to indicate that the bone fixation or retraction system has become unstable. This second threshold of movement may preferably be pre-set to be any amount greater than the first threshold, as desired. For example, the second threshold may be set to be on the order of 10 mm for translational movement or 10 degrees for rotational movement. When detected bone motion exceeds this second threshold of movement, it is preferable for safety reasons that the bone first be re-stabilized and that the surgical robotic cutting arm then be re-registered to the bone prior to re-starting bone cutting.

Measurement inaccuracies may exist in the surgical robotic arm such that movement of the surgical robotic arm to the locations of each of the marker pins may determine locations of these marker pins which do not correspond identically to the actual locations of the marker pins on the bone. Similarly, measurement inaccuracies may exist in the passive mechanical arm such that the bone motion detected by the movement of the passive mechanical arm does not correspond identically to the actual amount of bone movement.

Accordingly, the present invention also provides systems for separately determining the positional measurement accuracy for each of the surgical robotic arm and the passive mechanical arm bone motion detector. A separate transform relationship can be generated between the coordinate system of the surgical robotic arm and the coordinate system of the passive mechanical arm, such that the actual transform relationship can be verified and corrected. Accordingly, bone motion detected by the passive mechanical arm can be used to accurately update the registration between the surgical robotic arm and the bone, as follows.

The positional measurement accuracy of each of the surgical robotic arm and the passive mechanical arm is separately determined by moving the distal end of each respective arm into contact with a plurality of test structures which are disposed at known locations on a test fixture. Preferably, the test fixture will be immobilized with respect to the proximal ends of both the surgical robotic arm and the passive mechanical arm. For example, the test fixture could be mounted to the frame of the robotic workstation to which the proximal ends of the passive mechanical arm and surgical robotic arm are mounted.

Each of the surgical robotic arm and the passive mechanical arm will thus separately determine and record the locations of the test structures as the distal end of the respective arm is moved to sequentially contact each of the test structures. As such, a surgical robotic arm test data set comprising the locations of the test structures as determined by the surgical robotic arm, and a passive mechanical arm test data set comprising the locations of the test structures as determined by the passive mechanical arm will be generated.

By comparing the surgical robotic arm test data set with the known locations of the test structures, the positional measurement accuracy of the surgical robotic arm is determined. Similarly, by comparing the passive mechanical arm test data set with the known locations of the test structures, the positional measurement accuracy of the passive mechanical arm is determined. Having determined the measurement accuracy of both the passive mechanical arm and the surgical robotic arm with respect to a known fixed system of coordinates, it is then possible to generate a transformational relationship between the passive mechanical arm and the surgical robotic arm. As such, it is possible to accurately guide the surgical robotic arm as it operates on the bone, based upon bone motion detected by the passive mechanical arm. An advantage of determining the positional measurement accuracy of both the surgical robotic arm and the passive mechanical arm with a fixed test fixture is that both accuracy verification and determining the transform relationship between the surgical robotic arm and the passive mechanical arm are accomplished in a single step.

The present invention also includes a method of ceasing surgical bone cutting using a three degree-of-freedom bone motion detector such that translational movement of the bone in any of three mutually perpendicular axes beyond a minimum threshold distance will shut down bone cutting such that the spatial relationship between the surgical robotic cutting arm and the bone can be re-determined prior to re-commencing surgery.

The present invention also includes an apparatus for tracking and compensating for bone motion when operating on a bone, comprising; a surgical robotic arm, a bone motion tracking system and a computer for determining and updating registration between the surgical robotic arm and the bone in response to bone motion detected by the tracking system. In a preferred aspect, the bone motion tracking system is an articulated mechanical arm which is adapted to be secured at its distal end to the bone by a coupling member which is percutaneously fastened into the bone.

Preferably, the mechanical arm tracking system has six degrees-of-freedom of movement, being articulated with motion sensors being disposed to detect motion in one degree-of-freedom at each joint. Preferably, the surgical robotic arm and the bone motion tracking arm are both secured to the same fixed base, being the frame of a robotic workstation. As the distal end of the articulated mechanical arm moves with the bone, both translational and rotational movement of the bone can be detected.

An advantage of the present system is that by monitoring bone motion in six degrees of freedom, (ie: both translationally and rotationally), it is possible to identify and compensate for slight twisting or turning of the bone which could not be detected in a simple translational bone motion detector system.

In addition, a fixator device is also provided to hold the bone as stationary as possible during the cavity cutting procedure. The fixator is also preferably attached to the same fixed base from which the surgical robotic arm extends such that bone motion is minimized relative to the position of the surgical robotic cutting arm.

A test fixture having at least three reference points disposed at known locations thereon is also preferably included with the present system, and is preferably attached to the robotic workstation. The test fixture provides a device for verifying the positional measurement accuracy of the bone motion detector and the surgical robotic arm, as well as verifying the transform relationship between the two, as will be explained.

DESCRIPTION OF THE SPECIFIC EMBODIMENTS

The present invention tracks and compensates for bone motion such that cutting inaccuracies on the bone are minimized while the bone is being cut by a surgical robotic arm. In particular, the present invention is ideally suited for tracking and compensating for motion in a femur bone during robotically assisted total hip replacement, when a surgical cutting arm is drilling an implant cavity therein.

Figure 1:
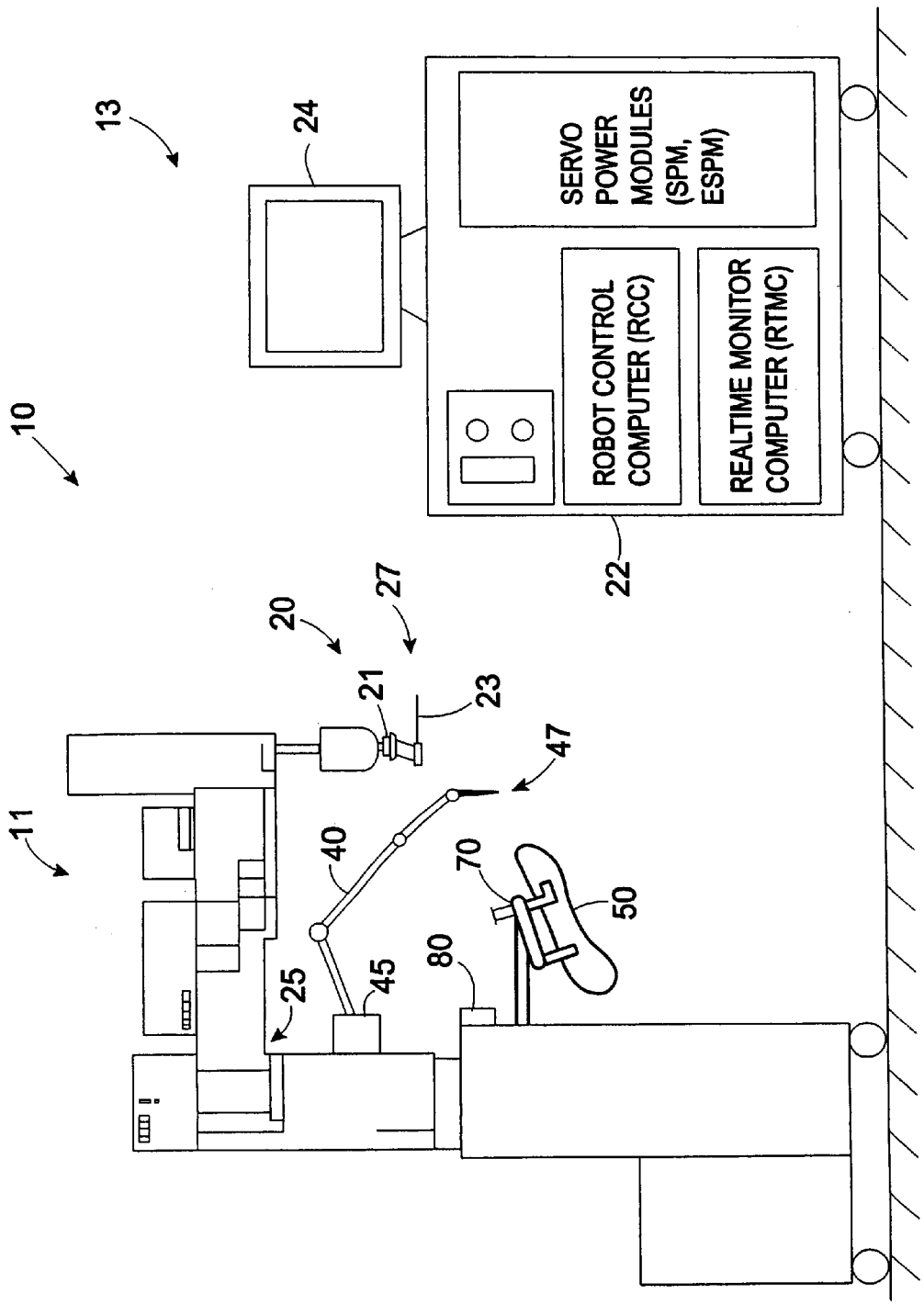
FIG. 1 is an illustration of the system of the present invention, showing a robot with a surgical robotic arm, a passive mechanical arm bone motion detector, a bone fixator, and a computer interface.

Referring to FIG. 1, robotic workstation 10 comprises a robot 11 and a user interface 13. Robot 11 further comprises a surgical robotic arm 20, a passive mechanical arm bone motion detector 40 and a bone fixator 70. Surgical robotic arm 20 can be any conventional manipulatable industrial robot preferably having at least 5 or 6 axes and capable of high precision motion. A suitable surgical robot is available from Sankyo Robotics with the model designation SR-5427-ISS. For use in the present invention, a force sensor 21 is mounted at the distal end of arm 20, and an effector in the form of a surgical cutting tool 23 may be attached to the force sensor. User interface 13 comprises a computer 22 and a terminal display 24.

Cutting tool 23 on surgical robotic arm 20 is adapted to cut an implant cavity into the end of femur bone 50. Fixator 70 is adapted to hold bone 50 in a substantially fixed position during surgery. Each of surgical robotic arm 20, passive mechanical arm 40 and fixator 70 are attached at their proximal ends to robot 11 which acts as a fixed base, preventing any relative motion between proximal ends 25 and 45 of surgical robotic arm 20 and passive mechanical arm 40, respectively.

Figure 2:
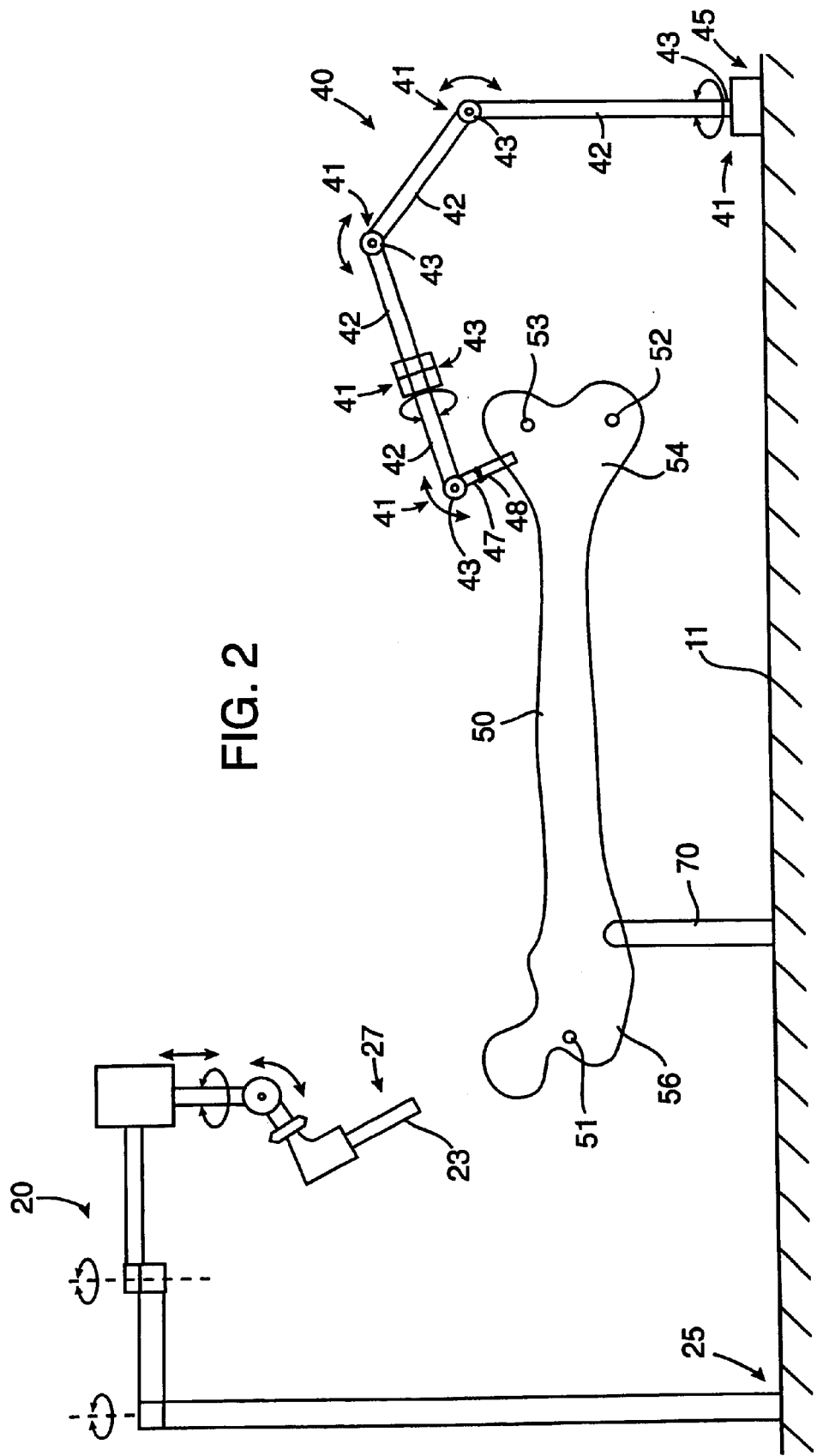
FIG. 2 is an illustration of a passive mechanical arm bone motion detector affixed to a femur bone, and a surgical robotic arm positioned adjacent the femur bone.

Referring to FIG. 2, further details of passive mechanical arm 40 can be seen. Passive mechanical arm 40 is preferably articulated, comprising a plurality of links 42 connected together at joints 41. Passive mechanical arm 40 has a proximal end 45 which is fixed to robot workstation 11 and a distal end 47 which is freely movable. A high resolution position sensor 43 is disposed in each joint 41. Using high resolution position sensors 43 and appropriate software, passive mechanical arm 40 can produce accurate measurements of the position of its distal end 47 with respect to proximal end 45 as distal end 47 is moved to various locations. Rotation of links 42 about joints 41 permits distal end 47 to be moved in any of 6 degrees of freedom relative to proximal end 45.

A bone coupling device 48 which is preferably percutaneously attached to bone 50 firmly anchors distal end 47 of passive mechanical arm 40 to bone 50. As illustrated, bone coupling device 48 can preferably be connected at the distal end 54 of the femur bone. Such connection permits surgical robotic arm 20 to operate at proximal end 56 of femur bone 50 without any interference between the respective arms. Bone coupling device 48 may comprise a bone screw which is preferably percutaneously attached to femur 50, thereby minimizing operative trauma.

As is also seen in FIG. 2, surgical robotic arm 20 is also adapted for movement in five or six degrees of freedom. Surgical robotic arm 20 has a proximal end 25 which is fixed to robot 11 and a distal end 27 which can be controllably moved to desired locations such that the position of movable distal end 27 relative to fixed proximal end 25 will be constantly known. Accordingly, by controllably moving distal end 27 of surgical robotic arm 20 to contact marker pins 51, 52 and 53, the position of each of the respective marker pins can be determined with respect to the position of the surgical robotic arm, (for reasons which will be explained).

Connection of both proximal end 45 of passive mechanical arm 40 and proximal end 25 of surgical robotic arm 20 to robot 11 avoids relative motion between ends 25 and 45, such that surgical robotic arm 20 and passive mechanical arm 40 move in the same relative coordinate system, the advantages of which will be explained.

The present invention provides a method of tracking and compensating for bone motion when surgical robotic arm 20 operates on bone 50 such that the correct positioning of surgical robotic arm 20 with respect to bone 50 can be maintained during the cutting operation, as follows.

In the preferred method, the surgical robotic arm 20 is first registered to bone 50, (ie: the spatial relationship between surgical robotic arm 20 and bone 50 is first determined). Such registration can be accomplished using a plurality of positioning marker pins 51, 52, and 53 which are first secured to bone 50 prior to surgery.

In a first approach to registration, a pre-surgical image is first taken of bone 50 with marker pins 51, 52 and 53 attached thereto. Distal end 27 of surgical robotic arm 20 is moved to sequentially contact each of marker pins 51, 52, and 53, recording their locations in the coordinate system of the surgical robotic arm. For example, distal end 27 of surgical robotic arm 20 is first advanced to contact pin 51. The location of pin 51 will thus be registered by surgical robotic arm 20. Surgical robotic arm 20 will then be advanced to locate pin 52, thereby registering the location of pin 52 with respect to surgical robotic arm 20. By sequentially advancing the surgical robotic arm to each of the three or more positioning pins 51, 52, and 53, the location of these pins is registered with respect surgical robotic arm 20. Since the spatial relationship between bone 50 and marking pins 51, 52 and 53 remains constant over time and has already been determined in a pre-surgical image, surgical robotic arm 20 is therefore registered to bone 50 by being registered to marker pins 51, 52 and 53. Having at least three positioning pins 51, 52, and 53, a coordinate system is defined for bone 50, enabling bone position and orientation to be determined in three dimensions.

Should such motion be detected during the initial registration of surgical robotic arm 20 to bone 50, the registration process can be automatically terminated such that the bone can be re-secured into position before the initial registration process is re-initialized. However, having passive mechanical arm 40 connected to bone 50 to monitor bone motion during the initial registration of surgical robotic arm 20 to bone 50 allows the initial registration process to be continuously updated, even during bone motion, such that it is not necessary to stop and recommence the initial registration procedure.

Specifically, when initially registering surgical robotic arm 20 to bone 50 by moving distal end 27 of surgical robotic arm 20 to contact each of marker pins 51, 52 and 53 in turn, bone motion may occur. For example, referring to FIG. 3, should bone 50 move to the position shown in phantom as bone 50a subsequent to the location of marker pin 51 being registered by surgical robotic arm 20, passive mechanical arm 40 will measure the exact amount and direction of bone motion occurring between bone 50 and bone 50a such that previously detected marker pin 51 can be translated in the coordinate system of the surgical robotic arm to the position shown as pin 51a. Alternatively, the location of pin 52a, (being the position of the marker pin as determined subsequent to bone motion), can be translated in the coordinate system of the surgical robotic arm to the position shown as 52, (being the position of the marker pin prior to bone movement). Accordingly, the locations of each of the marker pins 51, 52 and 53 can be updated in the coordinate system of surgical robotic arm 20 during the initial registration of surgical robotic arm 20 to bone 50.

As an alternative to using marker pins 51, 52, and 53 on bone 50, to register surgical robotic arm 20 to bone 50, it is also possible to use an optical, mechanical or ultrasound imaging system in conjunction with a pre-surgical image of bone 50 to determine the position and orientation of surgical robotic arm 20 with respect to bone 50 by the recognition of anatomical features thereon as described above. For example, sensor 80 may preferably comprise an optical or ultrasound system which determines the position and orientation of bone 50 by sensing anatomical features on the bone.

Alternatively, surgical robotic arm 20 can be registered to bone 50 without the use of marker pins 51, 52 and 53 by the system described in co-pending and recently allowed application Ser. No. 08/526,826 in which an image of bone 50 is transformed into-a robotic coordinate system by aligning a robotic probe within the medullary canal of the femur.

Alternatively, surgical robotic arm 20 can be registered to bone 50 without the use of marker pins 51, 52 and 53 by using passive mechanical arm 40 to generate a digitized bone data set by taking surface position measurements of bone 50 with passive mechanical arm 40, and transforming the bone image data set into the coordinate system of surgical robotic arm 20 by performing a best fit calculation between coordinates of a pre-surgical bone image data set and corresponding coordinates of the digitized bone data set. An example of such a system is described in co-pending application Ser. No. 09/152,359.

Once the surgical robotic arm 20 has been registered to bone 50, surgical robotic arm 20 can begin bone surgery. The problem of unwanted bone motion occurring during surgery, (after the spatial relationship between surgical robotic arm 20 and bone 50 has already been determined), is addressed by tracking bone motion with passive mechanical arm 40 attached to bone 50, as follows.

Figure 3:
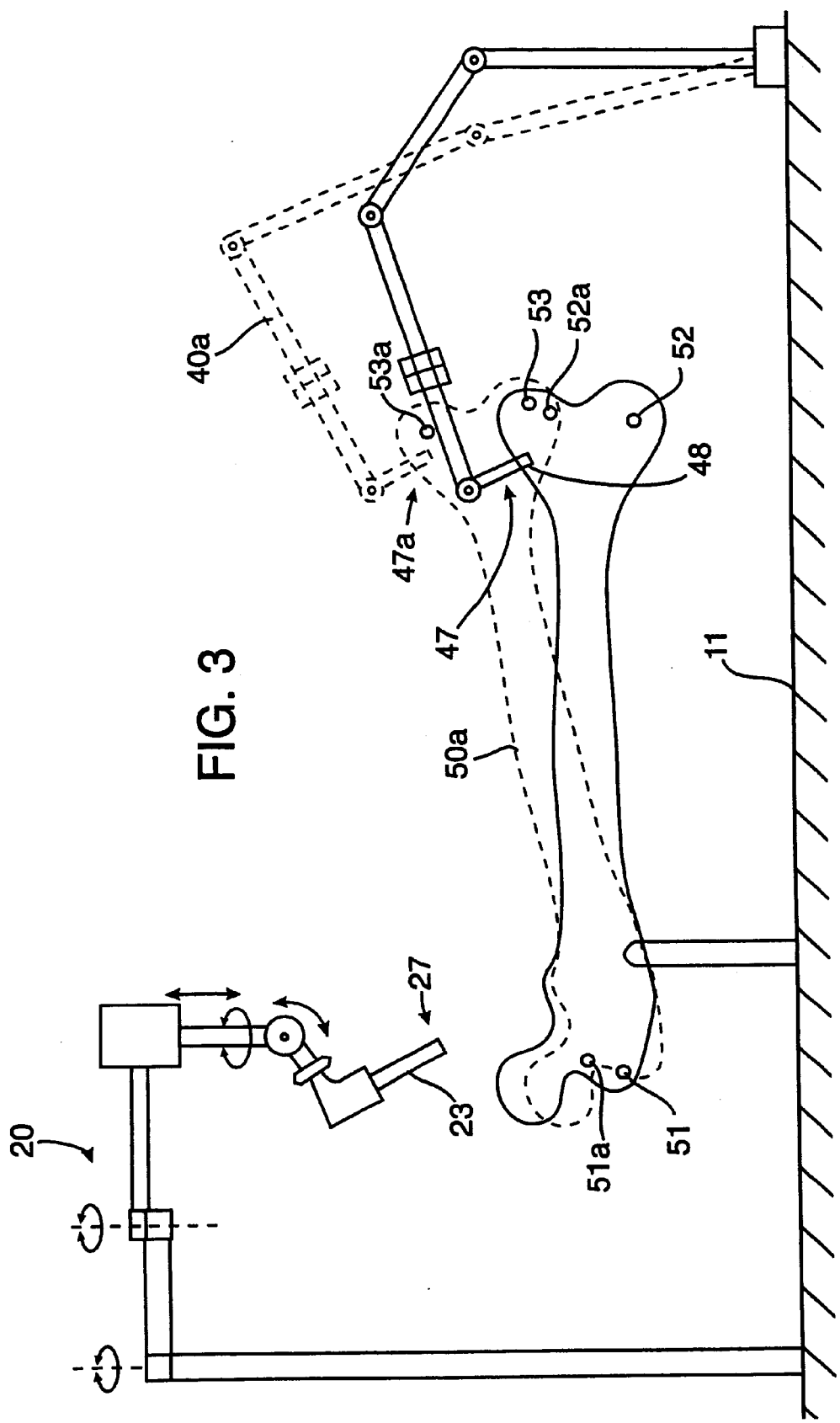
FIG. 3 is an illustration which corresponds to FIG. 2, but with the bone moved to a second position shown in phantom.

Since bone 50 and distal end 47 of passive mechanical arm 40 moves together as a solid unit, any motion will be detected by passive mechanical arm 40, (attached thereto at its distal end 47 by bone coupling device 48). As bone 50 moves through various combinations of three degrees of translational movement and three degrees of rotational movement, this motion will be tracked through identical movements of distal end 47 of passive mechanical arm 40. For example, FIG. 3 illustrates bone 50 moving to position 50a during bone cutting. As bone 50 moves to position 50a, passive mechanical arm 40 will move to the position illustrated by passive mechanical arm 40a.

When computer 22 detects that the amount of bone motion (as determined by the identical amount of movement of distal end 47 of passive mechanical arm 40), has reached a first pre-set threshold, computer 22 will update the registration between surgical robotic cutting arm 20 and bone 50.

As such, it is not necessary to monitor the positioning of positioning pins 51, 52, or 53 when tracking bone movement. Rather, any rotational or translational movements causing bone 50 to move to the position shown as bone 50a will be detected by a virtue the fixed connection between distal end 47 of passive mechanical arm 40 and bone 50a. The bone motion detected by passive mechanical arm 40 can thus be used to update the registration between surgical robotic arm 20 and bone 50a.

Various motion thresholds can be programmed into computer 22 such that the updating of the registration between surgical robotic arm 20 and bone 50 occurs as follows. For very small amounts of motion below a first threshold, bone motion is so minimal that no action need be taken. For example, the first threshold can be set for rotational movement on the order of ½ degree or translational movement on the order of ½ mm.

Should the cumulative movement of passive mechanical arm 40 exceed this first threshold, computer 22 will then correct for bone motion by updating the registration between surgical robotic arm 20 and bone 50. The cutting operation of surgical robotic arm 20 may optionally be paused during the period in which the registration is updated.

Should movement of passive mechanical arm exceed a second pre-set threshold, (which is greater than the first pre-set threshold of bone motion, and may comprise rotational movement on the order of 10 degrees or translational movement on the order of 10 mm), computer 22 will automatically terminate operation of surgical robotic cutting arm 20 for safety reasons as such large bone motion is indicative that the bone fixation has become unstable. Such movement beyond the second threshold may either be cumulative movement indicating the bone is drifting too far over a period of time, or alternatively, movement beyond the second threshold may be rapid movement over a shorter distance indicating that the bone fixation has become unstable.

The present invention also encompasses tracking the movement of distal end 47 in only three degrees of freedom (ie: translational movement in an X-Y-Z coordinate system), rather than in six degrees of freedom, (ie: translational and rotational movement in an X-Y-Z coordinate system).

The present invention also provides a novel system of determining the positional measurement accuracy of surgical robotic arm 20 and of passive mechanical arm 40 such that bone motion as detected by passive mechanical arm 40 can accurately be used to update the position of surgical robotic arm 20 with respect to bone 50 as follows.

Figure 4:
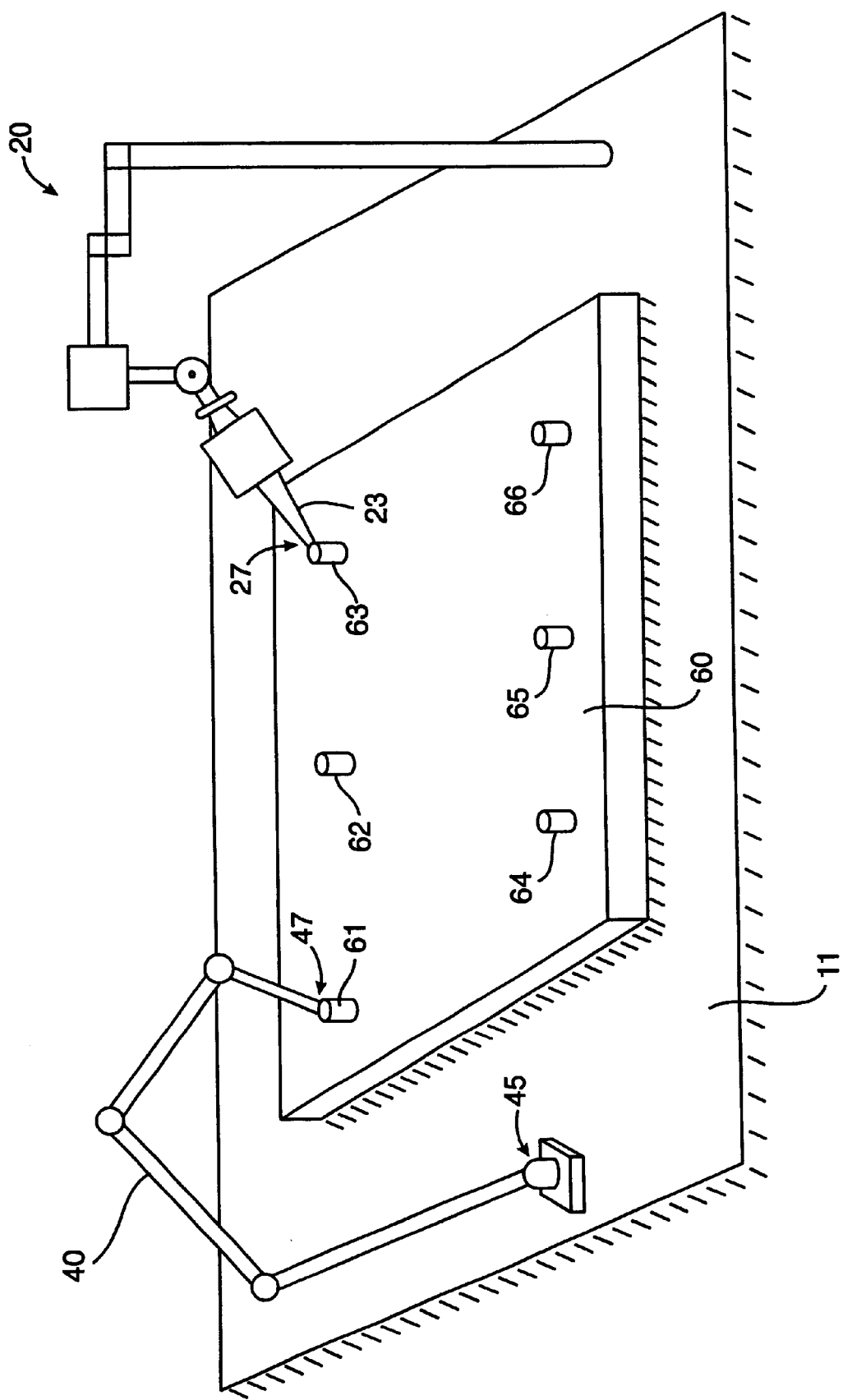
FIG. 4 is a schematic view of a test fixture for determining the positional accuracy of both the surgical robotic arm and the passive mechanical arm.

As is shown in FIG. 4, a test fixture 60 is also preferably secured to robot 11. Test fixture 60 preferably has a plurality of positioning structures 61, 62, 63, 64, 65, and 66 which are disposed at known locations on test fixture 60. Distal end 27 of surgical robotic arm 20 is moved into contact with each of test structures 61, 62, 63, 64, 65, and 66 in sequence, thereby generating a surgical robotic arm test data set comprising the locations of the test structures as determined by the surgical robotic arm. Similarly, distal end 47 of passive mechanical arm 40 is moved into contact with each of test structures 61, 62, 63, 64, 65, and 66 in sequence, thereby generating a passive mechanical arm test data set comprising the locations of the test structures as determined by the passive mechanical arm.

The actual spacing among each of the test structures with respect to one another is known when the test fixture is fabricated. Accordingly, each of the surgical robotic arm test data set and passive mechanical arm test data set can be compared to the known actual spacing among each of the test structures, thereby determining the accuracy of measurement of both the surgical robotic arm and the passive mechanical arm, respectively. Moreover, it is then possible to generate a transform relationship directly between passive mechanical arm 40 and surgical robotic arm 20 such that bone motion detected by passive mechanical arm 40 can accurately update the registration between surgical robotic arm 20 and bone 50.

By immobilizing test fixture 60 with respect to both surgical robotic arm 20 and passive mechanical arm 40, (such as by attaching test fixture 60 to robot 11), the accuracy of the verification of surgical robotic arm 20 and passive mechanical arm 40 is increased.

What is claimed is:

1. A method of tracking and compensating for bone motion when operating on a bone with a surgical robotic arm, comprising:

registering the surgical robotic arm to the bone with a six degree of freedom position sensor;

tracking movements of the bone with the six degree of freedom position sensor; and updating the registration as the bone moves.

2. The method of claim 1, wherein registering the surgical robotic arm to the bone comprises;

attaching a plurality of marker pins to the bone;

determining the spatial relationship of the bone to the plurality of marker pins; and registering the surgical arm to the plurality of marker pins secured to the bone.

3. The method of claim 2, wherein determining the spatial relationship of the bone to the plurality of marker pins comprises:

viewing a pre-surgical image of the bone with the plurality of marker pins attached.

4. The method of claim 1, wherein registering the surgical robotic arm to the bone comprises:

transforming a bone image data set representing an image of the bone into a robotic coordinate system of the surgical robotic arm by:

registering a bone digitizer arm to the robotic coordinate system, generating a digitized bone data set by taking bone surface position measurements with the digitizer arm, and transforming the bone image data set into the robotic coordinate system by performing a best fit calculation between coordinates of the bone image data set and corresponding coordinates of the digitized bone data set.

5. The method of claim 1, wherein, registering the surgical arm to the bone comprises;

comparing the position of the surgical arm to the position of anatomical features on the bone.

6. The method of claim 1, wherein, registering the surgical arm to the bone comprises;

aligning a probe on the surgical robotic arm with a medullary canal of a femur bone.

7. The method of claim 1 or 4, wherein, registering the surgical robotic arm to the bone; and tracking movements of the bone are performed simultaneously.

8. A method of tracking and compensating for bone motion when operating on a bone with a surgical robotic arm, comprising:

registering the surgical robotic arm to the bone tracking movements of the bone with a bone motion detector by:

securing a distal end of a six-degree-of-freedom mechanical arm to the bone; and tracking translational movement of the distal end of the mechanical arm as distal end of the mechanical arm moves with the bone; and updating the registration as the bone moves.

9. The method of claim 8, further comprising:

tracking rotational movement of the distal end of the mechanical arm as the distal end of the mechanical arm moves with the bone.

10. The method of claim 8 wherein securing the distal end of the mechanical arm to the bone comprises;

securing the distal end of the mechanical arm to the bone by a percutaneous coupling member.

11. The method of claim 10 wherein, the distal end of the mechanical arm is secured to the bone at a location spaced sufficiently apart from where the surgical robot arm operates on the bone, such that the mechanical arm does not interfere with operation of the surgical robotic arm.

12. The method of claim 1, wherein, tracking movements of the bone is done with an optical sensor.

13. The method of claim 1, wherein, tracking movements of the bone is done with an ultrasound sensor.

14. The method of claim 9, wherein, the registration is updated when the distal end of the mechanical arm has moved a first threshold amount.

15. The method of claim 1, 4 or 8, further comprising:

pausing operation of the surgical robotic arm concurrently with updating the registration.

16. The method of claim 14, further comprising:

ceasing operation of the surgical robotic arm when the distal end of the mechanical arm has moved by a second threshold amount, wherein the second threshold amount is greater than the first threshold amount.

17. The method of claim 1, 4 or 8, further comprising:

determining the accuracy of the surgical robotic arm by, moving a distal end of the surgical robotic arm to contact a plurality of test structures disposed at known locations on a test fixture to generate a surgical robotic arm test data set comprising coordinates corresponding to the locations of the test structures; and comparing the surgical robotic arm test data set to the known locations of the plurality of test structures on the test fixture.

18. The method of claim 8, further comprising:

determining the accuracy of the mechanical arm by, moving a distal end of the mechanical arm to contact a plurality of test structures disposed at known locations on a test fixture to generate a mechanical arm test data set comprising coordinates corresponding to the locations of the test structures; and comparing the mechanical arm test data set to the known locations of the plurality of test structures on the test fixture.

19. The method of claim 8, further comprising:

determining the accuracy of the surgical robotic arm by, moving a distal end of the surgical robotic arm to contact a plurality of test structures disposed at known locations on a test fixture to generate a surgical robotic arm test data set comprising coordinates corresponding to the locations of the test structures; and comparing the surgical robotic arm test data set to the known locations of the plurality of test structures on the test fixture; and determining the accuracy of the mechanical arm by, moving a distal end of the mechanical arm to contact a plurality of test structures disposed at known locations on a test fixture to generate a mechanical arm test data set comprising coordinates corresponding to the locations of the test structures;

comparing the mechanical arm test data set to the known locations of the plurality of test structures on the test fixture; and generating a transform relationship between the surgical robotic arm coordinate system and the mechanical arm coordinate system by comparing the surgical robotic arm test data set and the mechanical arm test data set.

20. A method of ceasing operation of a surgical robotic arm in response to bone movement, comprising:

registering the surgical robotic arm to the bone with a six degree of freedom position sensor;

tracking translational and rotational movement of the bone with the six degree of freedom position sensor; and ceasing operation of the surgical robotic arm when the six degree of freedom position sensor has detected a threshold amount of movement.

21. The method of claim 8, wherein, tracking translational movements of the bone with a bone motion detector comprises:

securing the distal end of a mechanical arm to the bone; and tracking translational movement of the mechanical arm in 3 degrees of freedom as the distal end of the mechanical arm moves with the bone.

22. A method of tracking and compensating for bone motion when operating on a bone with a surgical robotic arm, comprising:

(a) registering the surgical robotic arm to the bone by transforming a bone image data set representing an image of the bone into a robotic coordinate system of the surgical robotic arm by:

registering a bone digitizer arm to the robotic coordinate system, generating a digitized bone data set by taking bone surface position measurements with the digitizer arm, and transforming the bone image data set into the robotic coordinate system by performing a best fit calculation between coordinates of the bone image data set and corresponding coordinates of the digitized bone data set;

(b) tracking movements of the bone with a bone motion detector; and (c) updating the registration as the bone moves.

* * * * *